US006348605B1

United States Patent
Foguet et al.

(10) Patent No.: US 6,348,605 B1
(45) Date of Patent: Feb. 19, 2002

(54) PROCESS FOR PREPARING 3-HYDROXYMETHYL CHROMEN-4-ONES

(75) Inventors: Rafael Foguet; Jordi Bolos; Aurelio Sacristan; Josep M. Castello; José A. Ortiz, all of Barcelona (ES)

(73) Assignee: Ferrer Internacional, S.A., Barcelona (ES)

( * ) Notice: Subject to any disclaimer, the term of this patent is extended or adjusted under 35 U.S.C. 154(b) by 0 days.

(21) Appl. No.: 09/787,113

(22) PCT Filed: Sep. 20, 1999

(86) PCT No.: PCT/EP99/06946

§ 371 Date: Jun. 14, 2001

§ 102(e) Date: Jun. 14, 2001

(87) PCT Pub. No.: WO00/17183

PCT Pub. Date: Mar. 30, 2000

(30) Foreign Application Priority Data

Sep. 21, 1998 (ES) .............................................. 9801970

(51) Int. Cl.$^7$ ............................................. C07D 311/22
(52) U.S. Cl. ........................ 549/407; 549/408; 549/412
(58) Field of Search ................................. 549/407, 408, 549/412, 409

(56) References Cited

U.S. PATENT DOCUMENTS

| 2,378,573 A | 6/1945 | Natta |
| 3,887,584 A | 6/1975 | Von Strandtmann et al. |
| 5,643,927 A | 7/1997 | Foguet et al. |

FOREIGN PATENT DOCUMENTS

| WO | 9525733 A | 9/1995 |

OTHER PUBLICATIONS

Janos Borbely et al.; Tetrahedron, vol. 37, 1981, pp. 2307–2312.

*Primary Examiner*—Floyd D. Higel
*Assistant Examiner*—Kamal Saeed

(57) ABSTRACT

3-(Hydroxymethyl)chromen-4-ones of formula (I) are described and a process for preparing said compounds. The process consists in reacting the compounds of general formula (II) wherein R is hydrogen, halogen, alkyl having 1 to 4 carbon atoms or alkoxy having 1 to 4 carbon atoms optionally substituted by phenyl or halogen, with formaldehyde and a basic catalyst followed by dehydration in an acid medium to form 3-(hydroxymethyl)chromen-4-ones of general formula (I), wherein R is as defined for (II);

4 Claims, No Drawings

PROCESS FOR PREPARING 3-HYDROXYMETHYL CHROMEN-4-ONES

This application is the national phase under 35 U.S.C. § 371 of PCT International Application No. PCT/EP99/06946 which has an International filing date of Sep. 20, 1999, which designated the United States of America.

The present invention relates to 3-(hydroxymethyl) chromen-4-ones of general formula (I):

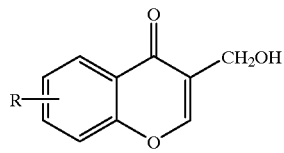

wherein R is hydrogen, halogen, alkyl having 1 to 4 carbon atoms or alkoxy having 1 to 4 carbon atoms optionally substituted by phenyl or halogen and to a new process for preparing said compounds.

The compounds of the present invention are useful as intermediates in the preparation of pharmaceuticals, such as those disclosed in WO 96/32389.

The processes in use for preparing the compounds of general formula (I) consist in:

a) Reduction of the corresponding 3-formylchromen-4-ones with $NaBH_4$ and $AlCl_3$ (Tetrahedron Letters, 1973, 1995; Tetrahedron, 1974, 3, 3553; Chem. Pharm. Bull., 1974, 22, 2959). These reactions have the inconvenience of resulting in a low yield.

b) Condensation of the corresponding 2-sulfinyl-acetophenones with two moles of HCHO and subsequent pyrolysis of the sulfoxide (J. Het. Chem., 1974, 11, 183). Unfortunately, there is a danger of explosion when sulfinylacetophenones are prepared on an industrial scale.

The process of the present invention consists in treating the compounds of general formula (II), wherein R is as defined for (I), with formaldehyde and catalytic amounts of basic compounds, as for example sodium acetate, followed by dehydration in an acid medium. Common mineral acids, such as hydrochloric acid, can be used as acidifying agents.

The compounds of general formula (II) are found in equilibrium with their open tautomer forms (II') and (II"). (Tetrahedron Letters, 1984, ad, 5813). Both in II' and in II" R is defined as for the preceding structures.

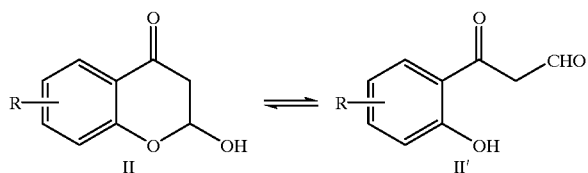

In contrast to the previously described processes, the process of the present invention provides high yields and, in addition, the industrial preparation of precursors is easily produced.

EXAMPLE 1

2-(Hydroxy)chromen-4-ones (II)

3.25 g (60 mmoles) of sodium methoxide, under a nitrogen atmosphere, were suspended in 60 mL of ethyl formate cooled to 0° C. The mixture was allowed to reach room temperature and was added dropwise a solution of the corresponding O-hydroxyacetophenone (III) (20 mmoles), wherein R is defined as for the preceding structures, in a minimal amount of tetrahydrofuran. The mixture was stirred for 30 minutes, and a stiff paste formed. 100 mL of water and 4.5 mL of acetic acid were added and stirred for 10 minutes, and the precipitate was dissolved. The organic phase was decanted and the aqueous phase was removed with further 40 mL of ethyl formate. The collected organic extracts were washed with two parts of 40 mL de sodium bicarbonate saturated solution, dried over anhydrous sodium sulfate and evaporated to dryness. The residue was suspended in 40 mL of diisopropyl ether, filtered and dried in vacuo to give the compounds of general formula (II).

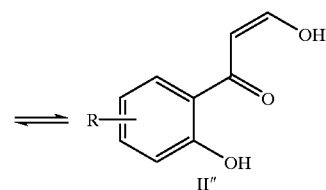

| R (II)          | Yield (%) | M.P.° (DSC) |
|-----------------|-----------|-------------|
| H               | 87        | 88.30       |
| 6-$CH_3$        | 100       | 136.03      |
| 7-$OCH_3$       | 85        | 139.44      |
| 6-$OCH_3$       | 92        | 146.61      |
| 6-Cl            | 93        | 160.62      |
| 7-$OCH_2Ph$     | 92        | 172.63      |
| 7-$O(CH_2)_3Cl$ | 80        | 118.23      |
| 7-$O(CH_2)_3Br$ | 69        | 104.95      |

EXAMPLE 2

3-(Hydroxymethyl)chromen-4-ones (I)

To a solution of 10 mmoles of (II) in 40 mL of acetone, 40 mg (0.5 umoles) of sodium acetate and 1 mL of 37% formaldehyde (12 mmoles) were added and stirred at room temperature for 2 hours. To this solution, 1 mL of concentrated hydrochloric acid was added and stirred at room temperature overnight. The solution was neutralized with a sodium acetate aqueous solution and evaporated to dryness in vacuo. 50 mL of water were added and then removed with two parts of 50 mL of ethyl acetate. The organic extracts were dried over anhydrous sodium sulfate and concentrated to a volume of about 15 mL. The product obtained was left to stand in a refrigerator overnight, and then crystallized and collected by filtration. The filtrate was washed with ethyl acetate and dried in vacuo to give the compounds of general formula (I).

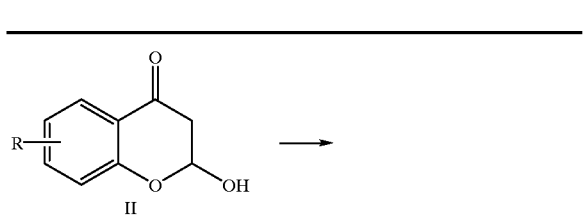

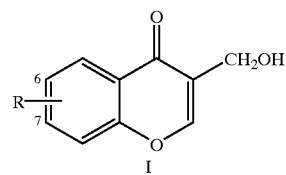

| R (I) | Yield (%) | M.P.° (DSC) |
| --- | --- | --- |
| H | 82 | 109.3 |
| 6-CH$_3$ | 70 | 143.7 |
| 7-OCH$_3$ | 78 | 119.98 |
| 6-OCH$_3$ | 80 | 151.8 |
| 6-Cl | 71 | 164.27 |
| 7-OCH$_2$Ph | 70 | 135.9 |
| 7-O(CH$_2$)$_3$Cl | 75 | 101.77 |
| 7-O(CH$_2$)$_3$Br | 75 | 105.38 |

What is claimed is:

1. A process for preparing 3-(hydroxymethyl) chromen-4-ones of formula (I):

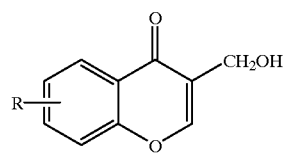

wherein R is hydrogen, halogen, alkyl having 1 to 4 carbon atoms or alkoxy having 1 to 4 carbon atoms optionally substituted by phenyl or halogen, which comprises treating the compounds of formula II

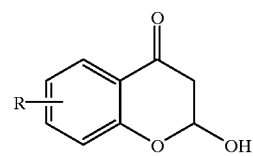

wherein R is as defined above, with formaldehyde and a basic catalyst followed by dehydration in an acid medium.

2. A process as claimed in claim 1 wherein sodium acetate is the basic catalyst.

3. A process as claimed in claim 1 wherein a mineral acid is used as an acidifying agent.

4. A process as claimed in claim 1 wherein hydrochloric acid is used as an acidifying agent.

* * * * *